(12) United States Patent
Loy et al.

(10) Patent No.: US 8,486,466 B2
(45) Date of Patent: Jul. 16, 2013

(54) **COMPOSITIONS COMPRISING *LILIUM SIBERIA* EXTRACTS AND USES THEREOF**

(75) Inventors: Chong Jin Loy, Singapore (SG); Khalid Mahmood, South Hadley, MA (US); Claude Saliou, Basking Ridge, NJ (US); Lijun Yu, Singapore (SG)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 204 days.

(21) Appl. No.: 12/971,512

(22) Filed: Dec. 17, 2010

(65) Prior Publication Data

US 2012/0156298 A1    Jun. 21, 2012

(51) Int. Cl.
*A61K 36/8967* (2006.01)

(52) U.S. Cl.
USPC ............ 424/773; 424/401; 424/725; 424/778

(58) Field of Classification Search
None
See application file for complete search history.

(56) References Cited

U.S. PATENT DOCUMENTS

| PP9,459 P | 2/1996 | Mak |
| 7,442,391 B2 | 10/2008 | Koganov |
| 7,473,435 B2 | 1/2009 | Koganov |
| 7,537,791 B2 | 5/2009 | Koganov |

OTHER PUBLICATIONS

Lily plant named Siberia, Johannes A. Mak, US patent; Plant 09,459; 1996.
Studies on the composition of the volatile oil from the flowers of *Lilium x siberia*. Zhang, Ji; Ma, Jun-yi; Yao, Jian; Yang et al., Xibei Zhiwu Xuebao (2003), 23(12). 2184-2187.

*Primary Examiner* — Susan Hoffman

(57) ABSTRACT

Provided are compositions comprising an extract of *Lilium siberia* and a carrier. Also provided are methods of lightening the skin comprising the step of applying to skin in need of skin lightening treatment an extract of *Lilium siberia*.

22 Claims, No Drawings

COMPOSITIONS COMPRISING *LILIUM SIBERIA* EXTRACTS AND USES THEREOF

FIELD OF INVENTION

The present invention relates to compositions comprising plant extracts for use on skin. More specifically, it relates to compositions comprising extracts of *Lilium siberia* for lightening the skin.

DESCRIPTION OF RELATED ART

A variety of products for lightening the skin are known in the art. In particular, products intended to lighten the skin, reduce uneven skin pigmentation and the appearance of pigmented spots (e.g. age spots, freckles, etc.), and/or otherwise treat conditions such as hyperpigmentation, discoloration, melasma, yellowing, and the like are known. However, many of such products are disadvantageous in that they tend to have low efficacy and/or exhibit undesirable toxicity or irritation in use. Accordingly, there is a need for new skin lightening materials.

*Lilium siberia* is a member of family Liliaceae with genus *Lilium*. The genus *Lilium* contains about 110 plants widespread all over the world. *Lilium siberia* is classified as a hybrid lily cultivar. According to Chinese literature [Zhao, Q; Li Q; Din, L & Lü, J; Studies on tissue culture and clonal propagation of Siberia, J. *Gansu Sciences*, (2003), 15(4), p 52-55], it is described to originate from *L. aurantum L.* and *L. seciosum* Thunb. The chemical diversity of *Lilium siberia* remains relatively unknown except for certain studies of the volatile components from its oil, see e.g., Zhang, J; Ma, J; Yao, J; Yang, Y; Zhao, X; Shang, B; Tao, M; Studies on the composition of the volatile oil from the flowers of *Lilium×Siberia*, *Xibei Zhiwu Xuebao* (2003), 23(12), 2184-2187. More recently, *Lilium siberia* was propagated asexually and is described with desirable characteristics of hybrid vigor, great hardiness, and a high degree of disease resistance, see Plant U.S. Pat. No. 09,459.

The present invention relates to the unexpected discovery that extracts of *Lilium siberia* (Oriental lily) plant are unexpectedly beneficial for inhibiting melanin synthesis in skin epidermal tissues and for lightening the skin.

SUMMARY OF THE INVENTION

Applicants have discovered unexpectedly that extracts of *Lilium siberia* may be used in compositions, preferably skin care compositions, and methods for skin lightening.

In particular, applicants have tested various *Lilium siberia* extracts and have discovered that such extracts exhibit significant and unexpected skin lightening properties. More specifically, as detailed in the Examples herein, applicants have measured the UVB-induced melanogenesis inhibition activity associated with *Lilium siberia* extracts and discovered that such extracts exhibit significant UVB-induced melanogenesis inhibition activity (known in the art to be associated with skin lightening). In addition, applicants have measured the lightening properties (ΔL) of the present extracts on skin equivalent materials and, as shown in the Examples, the extracts provided significant benefits in lightening the skin.

Accordingly, in one aspect, the present invention relates to compositions comprising extracts of *Lilium siberia* and a carrier.

In another aspect, the present invention relates to methods for lightening the skin by administering topically to a skin in need of such treatment, a composition comprising effective amounts of extracts of *Lilium siberia*.

DESCRIPTION OF THE INVENTION

As used herein, the term "lightening the skin" refers generally to lightening, brightening, whitening, and/or evening of the skin tone, skin color, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In certain embodiments, "lightening the skin" also refers to increased skin radiance, glow, translucency and/or luminescence and/or obtaining a more radiant, glowing, translucent or luminous skin tone appearance or a less yellow or sallow skin tone. In certain preferred embodiments, "lightening the skin" refers to lightening and evening the skin tone, increasing skin radiance and/or lightening age spots.

As used herein, the term "skin in need of skin lightening treatment" refers generally to skin that exhibits one or more property selected from the group consisting of: skin having a measured Individual Typology Angle (ITA) value below 41 as determined per the COLIPA GUIDELINE: GUIDELINE FOR THE COLORIMETRIC DETERMINATION OF SKIN COLOUR TYPING AND PREDICTION OF THE MINIMAL ERYTHEMAL DOSE (MED) WITHOUT UV EXPOSURE published in 2007, which is incorporated herein by reference and further described below, darkened and/or sallow skin, including skin darkened by UV, skin with uneven skin tone, or skin with one or more hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In the COLIPA guidelines, skin color is defined function of the ITA value as: very light skin >55; Light skin 41-55, Intermediate 28-41, and Tan skin <28. In certain preferred embodiments, "skin in need of skin lightening" refers to individuals with a skin having an ITA value of less than 41, such as about 40 or less, about 35 or less, about 30 or less, or more preferably about 28 or less. In certain other preferred embodiments, the present invention is directed to compositions and methods for use on skin in need of skin lightening treatment selected from sallow and/or darkened skin. In certain other preferred embodiments, the present invention is directed to compositions and methods for use on skin in need of skin lightening treatment selected from the group consisting of age spots, freckles, marks left after acne, and combinations of two or more thereof.

As used herein, unless otherwise specified, all percentages of ingredients in compositions are weight percent of active/solids ingredient based on the total weight of composition.

As used herein, a composition that is "essentially free" of an ingredient means the composition that has about 2% or less of that ingredient by weight based on the total weight of the composition. Preferably, a composition that is essentially free of an ingredient has about 1% or less, more preferably about 0.5% or less, more preferably about 0.1% or less, more preferably about 0.05 or less, more preferably about 0.01% or less by weight based on the total weight of composition of the ingredient. In certain more preferred embodiments, a composition that is essentially free of an ingredient is free of the ingredient, i.e. has none of that ingredient in the composition.

As used herein, "cosmetically/dermatologically acceptable" means that the ingredients which the term describes are suitable for use in contact with tissues (e.g., the skin or hair) without undue toxicity, incompatibility, instability, irritation, allergic response, and the like.

As used herein, the term "safe and effective amount" means an amount of the extract or of the composition sufficient to induce the desired effect, but low enough to avoid serious side effects. The safe and effective amount of the compound, extract, or composition will vary with e.g. the age, health and environmental exposure of the end user, the duration and nature of the treatment, the specific extract, ingredient, or composition employed, the particular pharmaceutically-acceptable carrier utilized, and like factors.

Any suitable extracts of the whole plant, flower, stem, leaves and/or bulb of *Lilium siberia* may be used in accord with the present invention. Suitable extracts may be derived from live or dried plant, small cuttings or other portions thereof, and the like.

Suitable extracts of *Lilium siberia* whole plant, flower, stem, leaves and/or bulb may be obtained using conventional methods including, but not limited to, direct extraction of material from the biomass by grinding, macerating, pressing, squeezing, mashing, centrifuging, and/or processes such as cold percolation, agitation/distillation, microwave assisted extraction, supercritical/subcritical $CO_2$ compressed gas extraction with or without polar modifiers, pressurized solvent extraction, accelerated solvent extraction, pressurized or normal hot water extraction, surfactant assisted pressurized hot water extraction, oil extraction, membrane extraction, Soxhlet extraction, the gold finger distillation/extraction and/or processes disclosed, for example, in U.S. Pat. Nos. 7,442,391, 7,473,435, and 7,537,791 to Integrated Botanical Technologies, LLC, incorporated herein by reference, and the like, or by other methods such as solvent extraction, and the like. Any of a variety of solvents including polar solvents, non-polar solvents, or combinations of two or more thereof may be used in methods of comprising solvent extraction. Suitable polar solvents include polar inorganic solvents such as water and the like, polar organic solvents such as alcohols and corresponding organic acids, for example $C_1$-$C_8$ alcohols including methanol, ethanol, propanol, butanol, and the like and organic acids, including acetic acid, formic acid, propanoic acid, and the like, polyols and glycols, including $C_1$-$C_8$ polyols/glycols and the like, and combinations of two or more thereof. Suitable non-polar solvents include non-polar organic solvents such as alkanes, including $C_1$-$C_8$ alkanes, cycloalkanes, including $C_1$-$C_8$ alkanes, alkyl ethers, including $C_1$-$C_8$ alkyl ethers, Petroleum ethers, ketones, including $C_1$-$C_8$ ketones, methylene chloride, ethyl acetate, xylene, toluene, chloroform, vegetable oil, mineral oil and the like. In another embodiment extraction may be obtained by non-polar solvents described above or supercritical fluid extraction with or without a polar modifier such as $C_1$-$C_8$ alcohols, water, $C_1$-$C_8$ polyols/glycols or $C_1$-$C_8$ organic acids.

In certain preferred embodiments, the extract comprises a non-polar extract prepared by extracting from fresh freeze dried flowers using a non-polar solvent comprising one or more $C_1$-$C_8$ alkanes, $C_1$-$C_8$ cycloalkanes, $C_1$-$C_8$ alkyl ethers, and/or chloroform, more preferably one or more $C_1$-$C_8$ alkanes and/or chloroform. In certain more preferred embodiments, the non-polar extract is extracted from *Lilium siberia* flower using hexanes, chloroform or a mixture thereof. In even more preferred embodiments, the non-polar extract is extracted from *Lilium siberia* flower using hexanes. In even more preferred embodiments, the non-polar extract is extracted from *Lilium siberia* flower using chloroform.

In certain preferred embodiments, the extract of the invention comprises a polar extract prepared by extracting from fresh freeze dried flowers using a polar solvent comprising water, $C_1$-$C_8$ alcohols, $C_1$-$C_8$ polyols, $C_1$-$C_8$ glycols, and combinations of two or more thereof. In certain more preferred embodiments, the polar extract is an aqueous extract extracted from *Lilium siberia* flower using water.

In certain other preferred embodiments, the extract of the invention comprises a combination of polar and non-polar extracts of from *Lilium siberia* flower.

In certain preferred embodiments, the extract comprises a non-polar extract prepared by extracting from *Lilium siberia* bulb using a non-polar solvent comprising one or more $C_1$-$C_8$ alkanes, $C_1$-$C_8$ cycloalkanes, $C_1$-$C_8$ alkyl ethers, and/or chloroform, more preferably one or more $C_1$-$C_8$ alkanes and/or chloroform. In certain more preferred embodiments, the non-polar extract is extracted from *Lilium siberia* bulb using hexanes, chloroform or a mixture thereof. In even more preferred embodiments, the non-polar extract is extracted from *Lilium siberia* bulb using hexanes. In even more preferred embodiments, the non-polar extract is extracted from *Lilium siberia* bulb using chloroform.

In certain preferred embodiments, the extract of the invention comprises a polar extract prepared by extracting from *Lilium siberia* bulb using a polar solvent comprising water, $C_1$-$C_8$ alcohols, $C_1$-$C_8$ polyols, $C_1$-$C_8$ glycols, and combinations of two or more thereof. In certain more preferred embodiments, the polar extract is an aqueous extract extracted from *Lilium siberia* bulb using water.

In certain other preferred embodiments, the extract of the invention comprises a combination of polar and non-polar extracts of from *Lilium siberia* bulb.

In certain preferred embodiments, the extract comprises a non-polar extract prepared by extracting from *Lilium siberia* stem using a non-polar solvent comprising one or more $C_1$-$C_8$ alkanes, $C_1$-$C_8$ cycloalkanes, $C_1$-$C_8$ alkyl ethers, and/or chloroform, more preferably one or more $C_1$-$C_8$ alkanes and/or chloroform. In certain more preferred embodiments, the non-polar extract is extracted from *Lilium siberia* stem using hexanes, chloroform or a mixture thereof. In even more preferred embodiments, the non-polar extract is extracted from *Lilium siberia* stem using hexanes. In even more preferred embodiments, the non-polar extract is extracted from *Lilium siberia* stem using chloroform.

In certain preferred embodiments, the extract of the invention comprises a polar extract prepared by extracting from *Lilium siberia* stem using a polar solvent comprising water, $C_1$-$C_8$ alcohols, $C_1$-$C_8$ polyols, $C_1$-$C_8$ glycols, and combinations of two or more thereof. In certain more preferred embodiments, the polar extract is an aqueous extract extracted from *Lilium siberia* stem using water.

In certain other preferred embodiments, the extract of the invention comprises a combination of polar and non-polar extracts of from *Lilium siberia* stem.

In certain preferred embodiments, the extract comprises a non-polar extract prepared by extracting from *Lilium siberia* leaves using a non-polar solvent comprising one or more $C_1$-$C_8$ alkanes, $C_1$-$C_8$ cycloalkanes, $C_1$-$C_8$ alkyl ethers, and/or chloroform, more preferably one or more $C_1$-$C_8$ alkanes and/or chloroform. In certain more preferred embodiments, the non-polar extract is extracted from *Lilium siberia* leaves using hexanes, chloroform or a mixture thereof. In even more preferred embodiments, the non-polar extract is extracted from *Lilium siberia* leaves using hexanes. In even more preferred embodiments, the non-polar extract is extracted from *Lilium siberia* leaves using chloroform.

In certain preferred embodiments, the extract of the invention comprises a polar extract prepared by extracting from *Lilium siberia* leaves using a polar solvent comprising water, $C_1$-$C_8$ alcohols, $C_1$-$C_8$ polyols, $C_1$-$C_8$ glycols, and combinations of two or more thereof. In certain more preferred embodiments, the polar extract is an aqueous extract extracted from *Lilium siberia* leaves using water.

In certain other preferred embodiments, the extract of the invention comprises a combination of polar and non-polar extracts of from *Lilium siberia* leaves.

Applicants have recognized for certain embodiments that preferred extracts of *Lilium siberia* comprise one or more polyunsaturated fatty acids having a structure of formula I:

R—COOH     (I)

wherein R is —$(CH_2)_z$—$(CH=CH-CH_2)_n$—$(CH_2)_m$—$CH_3$, where n is from 1 to 6, m is from zero to 6, and z is from 2 to 7. In certain preferred embodiments, R is selected from the group consisting of: —$(CH_2)_7$—$CH=CH-CH_2$—$(CH_2)_6$—$CH_3$, —$(CH_2)_7$—$(CH=CH-CH_2)_2$—$(CH_2)_3$—$CH_3$, —$(CH_2)_7$—$(CH=CH-CH_2)_3$—$CH_3$, and combinations of two or more thereof. In certain more preferred embodiments, the polyunsaturated fatty acids are omega-3, omega-6 or omega-9 fatty acids or combinations of two or more thereof. Examples of omega-3 fatty acids include, but are not limited to, 60-linolenic acid, eicosapentaenoic acid, docosahexaenoic acid, all-cis-6,9,12,15-octadecatetraenoic acid, Eicosatrienoic acid, Eicosatetraenoic acid, Clupanodonic acid, Nisinic acid, and the like. Examples of omega-6 fatty acids include, but are not limited to, linoleic acid, γ-linolenic acid, dihomo-γ-linolenic acid, arachidonic acid, Docosapentaenoic acid, Eicosadienoic acid, Docosadienoic acid, Adrenic acid, Calendic acid, and the like. Examples of omega-9 fatty acids include, but are not limited to, oleic acid, Erucic acid, Eicosenoic acid, Eicosatrienoic acid, and the like.

According to certain preferred embodiments, the extracts of *Lilium siberia* whole plant, flower, stem, leaves and/or bulb comprise at least about 0.005 weight % (wt. %) of one or more polyunsaturated fatty acids having a structure of formula I above. In certain embodiments, the extracts comprise from about 0.0051 to about 100 wt. % of polyunsaturated fatty acids having a structure of formula I, more preferably from about 1 to about 90 wt. % of polyunsaturated fatty acids having a structure of formula I, and even more preferably from about 40 to about 80 wt. % of polyunsaturated fatty acids having a structure of formula I. As described herein and claimed, the weight % of polyunsaturated fatty acids in an extract of *Lilium siberia* is calculated as weight of total solids content of all polyunstatured fatty acid(s) of Formula I in the extract divided by the weight of total solids content of the extract times 100 to get a percent.

According to certain preferred embodiments, the extracts of *Lilium siberia* whole plant, flower, stem, leaves, and/or bulb comprise one or more hydrophilic materials selected from the group consisting of polysaccharides, oligosaccharides, disaccharides, and combinations of two or more thereof. Examples of polysaccharides include, but are not limited to, Amylose, Amylopectin, Beta-glucans, Glycans, Xylan, Arabinoxylans, glucomannans, combinations of two or more thereof, and the like. Examples of oligosaccharides include, but are not limited to, trisaccharides such as raffinose, melezitose, maltotriose; tetrasaccharides such as acarbose, stachyose; pentasaccharides, combinations of two or more thereof, and the like. Examples of disaccharides include, but are not limited to, maltose, sucrose, lactose, trehalose, turanose, cellobiose, combinations of two or more thereof, and the like.

According to certain preferred embodiments, the extracts of *Lilium siberia* whole plant, flower, stem, leaves, and/or bulb comprise at least about 0.005 wt.% of one or more polysaccharides, oligosaccharides, disaccharides, and combinations of two or more thereof. In certain embodiments, the extracts comprise from about 0.01 wt.% to about 80 wt.% of polysaccharides, oligosaccharides, disaccharides, and combinations of two or more thereof, more preferably from about 1 to about wt. %, and even more preferably from about 10 to about 20 wt. % of polysaccharides, oligosaccharides, disaccharides, and combinations of two or more thereof.

In certain embodiments, the *Lilium siberia* whole plant, flower, stem, leaves, and/or bulb comprises one or more hydrophilic materials selected from the group consisting of amino acids, pyrroline derivatives, butanedioic acids and their esters, and combinations of two or more thereof. Examples of amino acids include, but are not limited to, threonine, tyrosine, cysteine, methionine, aspartic acid, asparagine, glutamic acid, glutamine, arginine, lysine, histidine, serine, glycine, valine, leucine, phenylalanine, tryptophan, proline, hydroxyproline, γ-aminobutyric acid, lanthionine, isoleucine, β-alanine, glycine, ornithine, hydroxylysine, and combinations of two or more thereof. In certain preferred embodiments, the *Lilium siberia* flower extract comprises the amino acid tyrosine. Examples of butanedioic acids and their esters include, but are not limited to malic acid, itatartaric acid, succinic acid, itaconic acid, hydroxyparaconic acids, their alkyl esters, and combinations of two or more thereof. Examples of pyrroline derivatives include, but are not limited to Ethyljatropham, Jatropham and its glucosides, Citraconimide, Pyrroline-2-one and its derivatives including glucosides, Lilaline, 3-methyl-1-(2-oxopyrrolidin-5-yl)-2,5-dihydropyrrol-2-one and its analogs.

According to certain preferred embodiments, the extracts of *Lilium siberia* whole plant, flower, stem, leaves, and/or bulb comprise at least about 0.001 wt. % of one or more amino acids, pyrroline derivatives, butanedioic acids and their esters, and combinations of two or more thereof. In certain embodiments, the extracts comprise from about 0.0011 to about 60 wt. % of amino acids, pyrroline derivatives, butanedioic acids and their esters, and combinations of two or more thereof, more preferably from about 0.01 wt. % to about 40 wt. %, and even more preferably from about 1 to about 20 wt. % of amino acids, pyrroline derivatives, butanedioic acids and their esters, and combinations of two or more thereof.

According to certain embodiments of the present invention, the *Lilium siberia* extract preferably comprises a solids weight ratio of lipophilic materials to hydrophilic materials of about 100:0 to about 10:90. As used herein, a "lipophilic material" generally refers to a material that has a dielectric constant of about 1 to about 15, preferably from about 2 to 15, at 22° C. (examples of lipohilic materials include, but are not limited to, (poly)saturated and unsaturated fatty alcohols/acids/esters and the like) and a "hydrophilic material" generally refers to a material that has a dielectric constant of greater than 15 to about 90, preferably greater than 15 to about 80, and in certain more preferred embodiments, from about 35 to about 80, at 22° C. (examples of hydrohilic materials include, but are not limited to, polysaccharides, oligosaccharides, disaccharides, amino acids, pyrroline derivatives, butanedioic acids and their esters, and the like). In certain more preferred embodiments, the extract of the present invention comprises a solids weight ratio of lipophilic materials to hydrophilic materials of about 90:10 to about 20:80 more preferably about 80:20 to about 40:60. In certain particularly preferred embodiments, the extract comprises a solids weight ratio of lipophilic materials to hydrophilic materials of about 80:20.

In certain embodiments, the *Lilium siberia* extract and/or the composition of the present invention may be prepared to have a relatively low amount of saturated fatty acids therein. In certain preferred embodiments, the extract is essentially free, more preferably free, of one or more saturated fatty acids. In addition, in certain preferred embodiments, the overall composition is essentially free, more preferably free, of one or more saturated fatty acids.

In certain preferred embodiments, the extract has a weight ratio of total polyunsaturated fatty acids of Formula I to total saturated fatty acids (total solids wt. polyunsaturated fatty acids: total solids wt. saturated fatty acids) of about 3:1 or greater. More preferably the weight ratio of total polyunsaturated fatty acids of Formula I to total saturated fatty acids in the extract is from about 4:1 to about 9:1 or greater. In certain more preferred embodiments, the weight ratio of total polyunsaturated fatty acids of Formula I to total saturated fatty acids is about 99:1 or greater.

In certain embodiments, the extract and/or compositions of the present invention may be essentially free of certain other materials. In one embodiment, the extract is essentially free of one or more flavanoids, saponins, and/or glucosides of flavanoids or saponins In certain embodiments, the extract and the resulting composition is essentially free of flavanoids, saponins and their glucosides. For example, in certain embodiments of the present invention a polar or non-polar extract may be further extracted with, for example, methanol to remove essentially all of the flavanoids, saponins, and/or glucosides of flavanoids or saponins, and/or may be subjected to chromatographical or other methods to remove such materials. Examples of flavanoids, saponins, and/or their glucosides include, but are not limited to: Luteolin, Apigenin, Sapogenin, rutinosides, Tangeritin, Quercetin, Kaempferol, 8-(3-Methylsuccinyl) kaempferol, Myricetin, Fisetin, Isorhamnetin, Pachypodol, Rhamnazin, Hesperetin, Naringenin, Eriodictyol, Etioline, Homoeriodictyol, Taxifolin (or Dihydroquercetin), Dihydrokaempferol, Genistein, Daidzein, Glycitein, epicatechin, 2-phenylethyl palmitate, Lilaline, Proanthocyanidins, 3,6'-diferuloylsucrose, Helonioside A, Isorhamnetin-3-rutinoside, Kaempferol-3-O-[b-D-xylopyranosyl-(1∴2)-b-D-glucopyranoside], Kaempferol-3-O-[b-D-glucopyranosyl-(1→2)-b-D-galactopyranoside], and the like.

Any suitable amounts of *Lilium siberia* whole plant, flower, stem, leaves, and/or bulb extract may be used in the compositions of the present invention. Preferably, the compositions comprise a safe and effective amount of *Lilium siberia* whole plant, flower, stem, leaves, and/or bulb extract. In certain preferred embodiments, the compositions comprise from greater than zero to about 20% *Lilium siberia* whole plant, flower, stem, leaves, and/or bulb extract. In certain other preferred embodiments, the compositions comprise from about 0.0001 to about 20%, from about 0.001 to about 10%, from about 0.01 to about 5%, from about 0.1 to about 5%, or from about 0.2 to about 2% *Lilium siberia* whole plant, flower, stem, leaves, and/or bulb extract. In certain other preferred embodiments, the compositions comprise from greater than zero to about 1%, from about 0.0001 to about 1%, from about 0.001 to about 1%, or from about 0.01 to about 1 *Lilium siberia* whole plant, flower, stem, leaves, and/or bulb extract. In certain other preferred embodiments, the compositions comprise from about 1 to about 5%, preferably from about 2 to about 5% *Lilium siberia* whole plant, flower, stem, leaves, and/or bulb extract. As used herein, unless otherwise specified, all percentages of ingredients in compositions are weight percent of active/solids ingredient based on the total weight of composition.

In certain preferred embodiments, the compositions of the present invention comprise a total weight percent of 0.001 to 20 wt. % (based on total weight of polyunsaturated fatty acids in the total weight of the overall composition) of polyunsaturated fatty acids having a structure of formula I (above). The polyunsaturated fatty acids of Formula I may be introduced to the composition as part of the *Lilium siberia* extract and/or may be introduced to the composition independent of the *Lilium siberia* extract. In preferred embodiments, the *Lilium siberia* extract in the composition comprises at least a portion of the polyunsaturated fatty acids of Formula I in the composition. In more preferred embodiments, the compositions of the present invention comprise a total weight percent of 0.01 to 10 wt. %, more preferably 0.1 to 5wt. %, and even more preferably 0.1 to 3 wt.% or 0.5 to 5wt. % of polyunsaturated fatty acids of Formula I.

Any suitable carrier may be used in the compositions of the present invention. Preferably, for a skin care composition, the carrier is a cosmetically-acceptable carrier. As will be recognized by those of skill in the art, cosmetically-acceptable carriers comprise carriers that are suitable for use in contact with the body, in particular the skin for skin whitening applications, without undue toxicity, incompatibility, instability, irritation, allergic response, and the like. A safe and effective amount of carrier is from about 50% to about 99.999%, preferably from about 80% to about 99.9%, more preferably from about 99.9% to about 95%, most preferably from about 99.8% to about 98% of the composition. The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cps to about 200,000 cps. Examples of suitable cosmetically-acceptable carriers include cosmetically-acceptable solvents and materials for cosmetic solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powered patches, microneedle patches, bandages, hydrogels, film-forming products, facial and skin masks, make-up, liquid drops, and the like. These product types may contain several types of cosmetically-acceptable carriers including, but not limited to solutions, suspensions, emulsions such as microemulsions and nanoemulsions, gels, solids, liposomes, other encapsulation technologies and the like. The following are non-limitative examples of such carriers. Other carriers can be formulated by those of ordinary skill in the art.

In one embodiment, the carrier contains water. In a further embodiment, the carrier may also contain one or more aqueous or organic solvents. Examples of organic solvents include, but are not limited to: dimethyl isosorbide; isopropylmyristate; surfactants of cationic, anionic and nonionic nature; vegetable oils; mineral oils; waxes; gums; synthetic and natural gelling agents; alkanols; glycols; and polyols. Examples of glycols include, but are not limited to, glycerin, propylene glycol, butylene glycol, pentalene glycol, hexylene glycol, polyethylene glycol, polypropylene glycol, diethylene glycol, triethylene glycol, capryl glycol, glycerol, butanediol and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol. The organic solvents may be present in the carrier in an amount, based upon the total weight of the carrier, of from about 1 percent to about 99.99 percent (e.g., from about 20 percent to about 50 percent). Water may be present in the carrier (prior to use) in an amount, based upon the total weight of the carrier, of from about 5 percent to about 95 percent (e.g., from about 50 percent to about 90 percent). Solutions may contain any suitable amounts of solvent, including from about 40 to about 99.99%. Certain preferred solutions contain from about 50 to about 99.9%, from about about 60 to about 99%, from about 70 to about 99%, from about 80 to about 99%, or from about 90 to 99%.

A lotion can be made from such a solution. Lotions typically contain at least one emollient in addition to a solvent. Lotions may comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s).

The compositions useful in the present invention can also be formulated as emulsions. If the carrier is an emulsion, from about 1% to about 10% (e.g., from about 2% to about 5%) of the carrier contains an emulsifier(s). Emulsifiers may be non-ionic, anionic or cationic.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or wipe). The composition of the present invention can also be combined with a solid, semi-solid or dissolvable substrate (eg., a wipe, mask, pad, glove or strip).

The compositions of the present invention may further comprise any of a variety of additional cosmetically active agents. Examples of suitable additional active agents include: additional skin lightening agents, darkening agents, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like. Examples of various suitable additional cosmetically acceptable actives include hydroxy acids, benzoyl peroxide, D-panthenol, UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate 0 (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinol palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as oat, aloe vera, Feverfew, Soy, Shiitake mushroom extracts, and derivatives and mixtures thereof.

In certain preferred embodiments, the compositions of the present invention are skin care compositions that comprise a *Lilium siberia* whole plant, flower and/or bulb extract and at least one additional skin lightening active agent. Examples of suitable additional skin lightening active agents include, but are not limited to, tyrosinase inhibitors, melanin-inhibiting agents, melanosome transfer inhibiting agents including PAR-2 antagonists, exfoliants, sunscreens, retinoids, antioxidants, Tranexamic acid, skin bleaching agents, allantoin, opacifiers, talcs and silicas, zinc salts, and the like, and other agents as described in Solano et al. Pigment Cell Res. 19 (550-571).

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, Dioscorea Coposita root extract, Saxifraga extract and the like, Ellagic acid, Salicylates and derivatives, Glucosamine and derivatives, Fullerene, Hinokitiol, Dioic acid, Acetyl glucosamine, Magnolignane, combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkylresorcinols such as 4-butyresorcinol (rucinol), 4-hexylresorcinol, phenylethyl resorcinol, 1-(2,4-dihydroxyphenyl)-3-(2, 4-dimethoxy-3-methylphenyl)-Propane and the like and natural extracts enriched in resorcinols. Examples of salicylates include, but are not limited to, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract,. In certain preferred embodiments, the melanosome transfer inhibiting agents includes a soy extract or niacinamide.

Examples of exfolliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfolliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol, retinaldehyde, retinoic acid, retinol palmitate, isotretinoin, tazarotene, bexarotene and Adapalene. In certain preferred embodiments, the retinoid is retinol.

Examples of antioxidants include, but are not limited to, water-soluble antioxidants such as sulfhydryl compounds and their derivatives (e.g., sodium metabisulfite and N-acetylcysteine, glutathione), lipoic acid and dihydrolipoic acid, stilbenoids such as resveratrol and derivatives, lactoferrin, and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, feverfew, parthenolide-free feverfew, oat extracts, pomelo extract, wheat germ extract, Hysperedin, Grape extract, Portulaca extract, Licochalcone, chalcone, 2,2'-dihydroxy chalcone, Primula extract, porpolis, and the like.

The additional cosmetically active agent may be present in a composition in any suitable amount, for example, in an amount of from about 0.0001% to about 20% by weight of the composition, e.g., about 0.001% to about 10% such as about 0.01% to about 5%. In certain preferred embodiments, in an amount of 0.1% to 5% and in other preferred embodiments from 1% to 2%.

A variety of other materials may also be present in the compositions of the present invention. These include, for example, chelating agents, humectants, opacifiers, conditioners, preservatives, fragrances and the like. The compositions may include surfactants, for example, those selected from the group consisting of anionic, non-ionics, amphoteric, cationic, or a combination of two or more thereof.

In certain preferred embodiments, the present invention is in the form of a substrate comprising a composition of the present invention. Any suitable substrate may be used in the present invention. Examples of suitable substrates and substrate materials are disclosed, for example, in U.S. Published Application Nos. 2005/0226834 and 2009/0241242 which are incorporated herein by reference in their entirety.

In certain preferred embodiments, the substrate is a wipe or a facial mask. Preferably, such embodiments comprise a water-insoluble substrate as such is defined in the cited references above. For certain embodiments, the water-insoluble substrate may have a size and shape such that it covers the face of a human user to facilitate placing the water-insoluble substrate about the face of the user as a mask substrate. For example, the water-insoluble mask substrate may have openings for a mouth, nose, and/or eyes of the user. Alternatively, the water-insoluble substrate may have no such openings. Such a configuration without openings may be useful for embodiments of the invention in which the water-insoluble substrate is intended to be draped over a non-facial expanse of skin or if the water-insoluble substrate is intended to be used as wipe. The water-insoluble substrate may have various shapes, such as an angular shape (e.g., rectangular) or an arcuate shape such as circular or oval.

In one embodiment of the invention, the product includes a plurality of water-insoluble substrates of different shapes. In one embodiment of the invention, the product includes a first water-insoluble substrate and a second water-insoluble substrate. The first water-insoluble substrate is shaped for application onto the forehead and the second water-insoluble substrate is shaped for application proximate to the mouth, such as areas above and/or below the lips, the chin, and/or the cheeks. In one embodiment of the invention, the first water-insoluble substrate is also applied to the nose region of the face. The first water-insoluble substrate may have a surface area of from about 100 cm$^2$ to about 200 cm$^2$, such as from about 120 cm$^2$ to about 160 cm$^2$ and the second water-insoluble substrate has a surface area of from about 100 cm$^2$ to about 300 cm$^2$, such as from about 150 cm$^2$ to about 250 cm$^2$. In one embodiment of the invention, the water-insoluble substrate has a low stiffness such that it may, for example, readily drape over or conform to the face or other body parts of the user.

The present invention further comprises methods of lightening the skin by applying to skin in need of skin lightening treatment an extract of *Lilium siberia* whole plant, flower, stem, leaves, and/or bulb, as such extracts and embodiments thereof are described above. In certain embodiments, the method comprises applying a composition of the present invention comprising an extract of *Lilium siberia* whole plant, flower, stem, leaves, and/or bulb, as such compositions are described above in various embodiments, to skin in need of skin lightening treatment.

The present invention may comprise application to any skin in need of treatment on the body. For example, application may be made to any one or more of the skin of the face, neck, chest, back, arms, axilla, hands and/or legs.

Preferably, the methods of the present invention comprise applying a safe and skin-lightening effective amount of *Lilium siberia* whole plant, flower, stem, leaves, and/or bulb extract to the skin. In certain preferred embodiments, the methods comprise applying from greater than zero to about 20% *Lilium siberia* extract to the skin in need. In certain other preferred embodiments, the methods comprise applying from about 0.0001 to about 20%, from about 0.001 to about 10%, from about 0.01 to about 5%, from about 0.1 to about 5%, or from about 0.2 to about 2% *Lilium siberia* extract to the skin in need. In certain other preferred embodiments, the methods comprise from greater than zero to about 1%, from about 0.0001 to about 1%, from about 0.001 to about 1%, or from about 0.01 to about 1% *Lilium siberia* extract to the skin. In certain other preferred embodiments, the methods comprise applying from about 1 to about 5%, preferably from about 2 to about 5% *Lilium siberia* extract to the skin.

Any suitable method of applying the extract to the skin in need may be used in accord with the present invention. For example, the extract may be applied directly from a package to the skin in need, by hand to the skin in need, or may be transferred from a substrate such as a wipe or mask, or a combination of two or more thereof. In other embodiments, the extract may be applied via a dropper, tube, roller, spray, patch or added to a bath or otherwise to water to be applied to the skin, and the like.

In certain embodiments, the methods of the present invention further comprise the step of leaving the *Lilium siberia* whole plant, flower and/or bulb extract in contact with the skin for period of time. For example, in certain preferred embodiments after application, the extract is left in contact with the skin for a period of about 15 minutes or greater. In certain more preferred embodiments, the extract is left in contact with the skin for about 20 minutes or greater, more preferably about 1 hour or greater.

In certain embodiments, the method of the present invention comprises a regimen comprising applying the *Lilium siberia* whole plant, flower and/or bulb extract to skin multiple times over a selected period of time. For example, in certain embodiments, the present invention provides a method of skin lightening comprising applying to skin in need of skin lightening a composition comprising a *Lilium siberia* whole plant, flower and/or bulb extract once or twice daily for at least 12 weeks, preferably at least 8 weeks and more preferably for at least 2 weeks.

In certain preferred embodiments, the methods of the present invention comprise applying at least two different compositions or products comprising *Lilium siberia* whole plant, flower and/or bulb extract to the skin. For example, the methods may comprise applying a first composition comprising *Lilium siberia* whole plant, flower and/or bulb extract to skin in need of skin lightening followed by applying a second composition comprising *Lilium siberia* whole plant, flower and/or bulb extract, but that is otherwise different from the first composition, to the skin in need of skin lightening. In certain preferred embodiments, the first and second composition may be independently selected from the group consisting of lotions, cleansers, masks, wipes, creams, serums, gels, and the like. In certain preferred embodiments, at least one of the first and second compositions is a cleanser, lotion, cream, essence, or serum and the other is a facial mask or wipe. In certain other preferred embodiments, at least one of the first and second compositions is a cleanser and the other is a lotion or cream.

In certain other preferred embodiments, the method comprises applying at least three products comprising *Lilium siberia* whole plant, flower and/or bulb extract to skin in need of skin lightening. Preferably such three products are selected from the group consisting of cleansers, lotions, creams, essences, and facial masks.

EXAMPLES

The following test methods were used in the Examples:
Melanin Synthesis Inhibition Test Control samples of B16(F10) murine melanoma cells were prepared and harvested as indicated below, but without addition of any test sample and without exposure to UVB (untreated control). Other control samples were prepared and harvested as indicated below without addition of test sample and exposed to UVB as described below (treated control). One or more samples of B16(F10) cells were prepared and each pre-treated with a test sample (e.g. E1) followed by UVB exposure as described below. Upon treatment, UVB stimulated melanogenesis in the cells and test compounds were evaluated based on their ability to inhibit or slow down the rate of melanogenesis. The cells were lysed for protein measurement at 595 nm and melanin content at 470 nm. The potency of the test compounds were determined by comparing the % inhibition achieved by the test compounds against the treated control.

Testing Procedure:

On a first day, murine melanoma B16(F10) cells were seeded in 60mm plates with a density of ~1 million cells per plate and incubated for 48hrs at 37° C., 5% $CO_2$. On day 2, the cells with a confluency rate of 90-100% were treated with test compound at a predetermined concentration (e.g. 25 µg/mL) for two hours (for test compound samples only) followed by exposure to UVB 20 mJ/cm$^2$ (for test samples and treated control). The cells were harvested on day 3 (24 h post UVB irradiation for test samples and treated control) and lysed in protein lysis buffer (50 mM Tris, pH 8, 2 mM EDTA, 150 mM NaCl, and 1% Triton X 100—a nonionic surfactant purchased from BioRad Cat. #: 161-0407), and centrifuged. The resulting supernatant was mixed well with a protein dye assay (Bio-rad protein assay reagent) and a spectrophotometer (Molecular Devices VERSAmax) was used to determine the optical density (protein assay OD) of the sample at 595 nm. The cell pellet remaining after removal of the supernatant was dissolved in alkaline DMSO buffer, and the resulting solution used for melanin absorbance assay at 470 nm to determine melanin assay OD.

Three samples each of the untreated control, treated control, and each test sample were made and the Melanin and Protein OD measured for each. The normalized melanin for each untreated control (3 samples), treated control (3 samples) and test sample (3 samples for each test compound) was calculated via the following equation:

Normalized Melanin=melanin assay OD/protein assay OD.

The average normalized Melanin of the untreated controls was calculated (sum of the three calculated values/3), and the average normalized Melanin of the treated controls similarly calculated.

The Induction value of the Control was calculated via the equation:

Induction value of Control=average normalized Melanin of treated control–average normalized Melanin of untreated control.

The Induction value with each test sample is then calculated via the equation:

Induction value with Test Sample=normalized Melanin of the test sample–average normalized Melanin of untreated control.

The Inhibition % for each test sample is then calculated via the equation:

100×[(Induction value of Control–Induction value with Test Sample)/Induction value of Control]. The average Inhibition % is calculated as the sum of the three resulting Inhibition % values for each test sample divided by three.

The calculation sequence for % inhibition are explained by a theoretical example, see the following table.

| | |
|---|---|
| Average normalized melanin Untreated control | 0.98 |
| Average normalized melanin UVB treated control | 2.56 |
| Induction value of control | 2.56 − 0.98 = 1.58 |
| Average normalized melanin Test sample | 1.04 |
| Induction value with Test sample | 1.04 − 0.98 = 0.06 |
| Inhibition % for Test sample | [(1.58 − 0.06)/1.58] × 100 = 96.20% |

Skin Epidermal Equivalents Model as a skin Lightening Test ($\Delta L$)

Skin epidermal equivalent tissues are available commercially from MatTek's MelanoDerm™ System and were used for the following tests. MatTek's MelanoDerm™ System consists of normal, human-derived epidermal keratinocytes (NHEK) and melanocytes (NHM) which have been cultured to form a multilayered, highly differentiated model of the human epidermis. Specifically, MEL-300-B tissues, each 9 mm in diameter were used in the following tests.

The test materials prepared in an appropriate vehicle and tested concentrations were applied topically to the skin model daily and the experiment lasted for 8 days. Measurement was taken on day 9.

The macroscopic and microscopic visual tissue darkening end points were measured by taking pictures with a digital camera. The Degree of Lightness for each tissue (L-Value) was measured using a spectrophotometer (Konica Minolta CM-2600d). The $\Delta L$ (degree of lightness as compared to control) for each test sample is calculated as per following formula:

$\Delta L = L$-value of treated sample–$L$-value of control sample.

According to certain preferred embodiments, the compositions of the present invention are effective to achieve a $\Delta L$ in accord with this test of greater than zero. More preferably, the compositions of the present invention are effective to achieve a $\Delta L$ of about 0.15 or greater, more preferably about 0.5 or greater, more preferably about 1 or greater, more preferably about 1.5 or greater, and more preferably about 2 or greater.

Cell Viability Test

Cell Viability of the tissue during experiment was evaluated using the MTT assay described as follows. The MTT Tissue Viability Assay is a colorimetric assay system that measures the reduction of a yellow Methylthiazolyldiphenyl-tetrazolium bromide (MTT) into an insoluble purple product by the mitochondria of viable cells.

The skin epidermal tissues used previously to determine degree of lightness for each test material and of untreated tissues were used to determine percent viable cells remaining at the end of the experiment. The skin epidermal tissues after degree of lightnes test were incubated with MTT reagent for 3 h. After incubation extraction buffer is added to lyse the cells and allowed to continue overnight. Samples are read using a plate reader at a wavelength of 570 nm and compared against untreated control and expressed in %Cell Viability as of control. A reduction of $\geq 30\%$ cell viability as of control consider as a significant indication of cell cytotoxicity caused by the test materials. The amount of purple color produced is directly proportional to the number of viable cells.

Example 1

Preparation of *Lilium siberia* Flower Extracts (E1-E4 and E2'-E3')

The extracts were prepared as follows: dry powder of *Lilium siberia* flowers (available from Layn Natural Ingredients) was suspended with solvent (as shown in Table 1) in an approximate 1:10 ratio (raw material/solvent). The suspension was stirred for 12 h at room temperature. The supernatant was then removed by filtration. Solvent was evaporated under reduced pressure in an evaporator at 30-40 deg C.

TABLE 1

E1-E4 extracts obtained from *Lilium siberia* flower dry powder.

| Flower Extract | Solvent |
|---|---|
| E1 | Hexane |
| E2 | Water |
| E3 | Methanol |
| E4 | Chloroform |

HPLC analysis of E1 and E4 revealed that they are mainly composed of lipids (at least 50% or more), specifically unsaturated omega fatty acids and their esters. A number of omega fatty acids and saturated fatty acids identified from E1 & E4 include Linoleic acid, Linolenic acids, triglycerides, and palmitic acid. Extracts E2 and E3 are mainly composed of polar components with no or very little lipids.

Extracts E2'-E3' were prepared as follows: *Lilium siberia* flowers dry powders were extracted with hexanes and removed to get a "defatted" flower material. The defatted flower materials was then extracted with water or methanol (as indicated in Table 2) for 12 h at room temperature. The supernatant was removed by filtration and treated with charcoal to remove excessive colored materials, filtered and dried. HPLC analyses provide no significant difference of compositions of E2' and E3' as compared to E2 and E3 respectively.

TABLE 2

*Lilium siberia* flower extracts

| Flower Extract | Solvent |
|---|---|
| E2' | Water |
| E3' | Methanol |

Example 2

Preparation of *Lilium siberia* Bulb Extracts (E5-E8)

The extracts were prepared as follows: dry powder of the bulb of *Lilium siberia* (available from Layn Natural Ingredients) were suspended with solvent (as shown in Table 3) in an approximate 1:10 ratio (raw material/solvent). The suspension was stirred for 12 h at room temperature. The supernatant was then removed by filtration. Solvent was evaporated under reduced pressure in an evaporator at 30-40 deg C.

TABLE 3

E5-E8 extracts obtained from *Lilium siberia* bulb dry powder.

| Bulb Extract | Solvent |
|---|---|
| E5 | Hexane |
| E6 | Water |
| E7 | Methanol |
| E8 | Chloroform |

HPLC analysis of E5 and E8 revealed that they are mainly composed of lipids (at least 50% or more), specifically unsaturated omega fatty acids and their esters. Extract E8 is mainly composed of one major unidentified component eluted after most of other omega fatty acids. A number of omega fatty acids and saturated fatty acids identified from E5 & E8, e.g. Linoleic acid, Linolenic acids, triglycerides, and palmitic acid. Extracts E6 and E7 are mainly composed of polar components with no or very little lipids.

Example 3

Preparation of *L. Siberia* Bulb or Flower Serum Extracts

In another example plant serum extracts are prepared from whole bulb or whole flower cell juice. The detailed method of extraction is published in patent literature U.S. Pat. No. 7,442,391 B2. This method provides a unique opportunity to maximize the melanogenesis inhibition by selectively concentrating desired bioactives in one extract.

Example 4

Determination of Melanin Synthesis Inhibition Activity

Extracts E1-E8 were tested in B16 cells for UVB induced melanin synthesis inhibition in accord with the Melanin Synthesis Inhibition Test. The bioactivity data as IC50 values for extracts El-E8 are listed in Table-4.

TABLE 4

UVB Induced Melanin Synthesis Inhibition Data

| Extract | Part of *L. Siberia* used | UVB Melanin Synthesis Inhibition, IC50 (μg/mL) |
|---|---|---|
| E1 | Flower | 40 |
| E2 | Flower | 200 |
| E3 | Flower | 100 |
| E4 | Flower | 40 |
| E5 | Bulb | 6 |
| E6 | Bulb | 80 |
| E7 | Bulb | 80 |
| E8 | Bulb | 9 |

Extracts E1-E8 were tested for mushroom tyrosinase enzyme inhibition up to 0.1% and found no significant activity for any extract.

Example 5

Determination of Melanin Synthesis Inhibition Activity in skin Epidermal Equivalent Model E4 was tested (at the concentrations listed in Table 5) for its skin lightening efficacy in accord with the Skin Epidermal Equivalents Model as a skin Lightening Test (ΔL). The test results confirmed the lightening efficacy of E4 and the data are recorded in Table 5.

TABLE 5

Degree of Lightness

| Extract | Plant Part used | Conc. Used (%) | Degree of Lightness (L value) | Standard Deviation |
|---|---|---|---|---|
| E4 | Flower | 2 | 0.36 | 0.17 |
|  |  | 5 | 1.9 | 0.2 |

Example 6

Preparation of Composition

A typical product formula in cream with skin lightening actives from *Lilium siberia* is made using the ingredients in Table 6 as follows.

TABLE 6

| Item # | Ingredient/ Function | Trade/INCI Name | % Weight |
|---|---|---|---|
| 1 | Purified Water | Water | Balance |
| 2 | EDTA BD | Disodium EDTA | 0.10 |
| 3 | Emulsifiers | Pemulen TR-1, Brij72, Brij 721, Lanette 22, Amphisol K, Simulgel EG | 4.90 |
| 4 | Thickeners | Carbopol Ultrez 20, Xanthan gum 180 | 0.20 |
| 5 | Humectants | Butylene Glycol, Glycerin | 9.00 |
| 6 | Skin Conditioning Agent | Prodew 300, Cetiol SB-45, Edenor ST 1 MY, Miglyol 812N, Finsolve TN, DC 200 50 cps, DC 345 Fluid, DC 1403, SP-500 | 15.75 |
| 7 | Chlorohexidine Digluconate 20% | Chlorohexidine Digluconate | 0.25 |

TABLE 6-continued

| Item # | Ingredient/ Function | Trade/INCI Name | % Weight |
|---|---|---|---|
| 8 | Oriental lily Extract | Lilium Siberia flower extract | 1.00 |
| 9 | Preservatives | Methyl Paraben, Ethyl paraben, Propyl Paraben | 0.60 |
| 10 | Neutralizing Base | Sodium hydroxide | As per need |
| 11 | Hydrolite-5 | Pentylene Glycol | 1.00 |

The ingredients are mixed as per standard procedures. A brief general procedure is described here for guidance.

Premix A: Dissolve *Lilium siberia* flower extract in butylene glycol and water

Premix B: Mix Glycerin and Xanthan 180 until a uniform mixture is achieved

Premix C: Disperse SP 500 in Butylene glycol

Water Phase:
  Add water into the vessel, begin agitation, add EDTA BD and mix until uniform
  Sprinkle in Pemulen TR-1 and Carbopol Ultrez 20 and mix until a translucent mixture is obtained
  Add Prodew 300, Butylene glycol, and Xantural Premix B until uniform
  Start heating to 80-83° C.
  At 70-75° C., add methyl paraben and mix until uniform
  At 80° C., add sodium hydroxide to neutralize the water phase, Hold Temperature until phasing Oil Phase:
  Mix Miglyol 815, Finsolve TN, Lanette 22, Edenor ST1 MY, Brij 721, Cetiol SB45, Ethyl paraben, Propyl paraben, and heat to 80° C., check that a clear melt is achieved before mix for 20 minutes. At 80° C., add Amphisol K and mix until uniformly dispersed. Hold the temperature at 80-83° C. until phasing.

Phasing:
  Add Oil phase to water phase under homogenization
  Add Simulgel EG and mix until uniform. Do not proceed until thickening effect is observed.
  Start Cooling to 60-65° C.
  At 60-65° C., slowly add Premix A.
  At 55-60° C., add DC 200 50 cst, DC 345 and DC 1403 and mix until uniform
  At 45° C., add Premix C
  At below 35° C., add Hydrolite 5, Chlorohexidine digluconate, and mix until uniform and homogenize the batch for 5 minutes.

What is claimed is:

1. A method of lightening the skin comprising applying to skin in need of skin lightening treatment an effective amount of an extract comprising a *Lilium siberia* flower extract, a *Lilium siberia* bulb extract, or a combination thereof.

2. The method of claim 1 wherein said extract comprises a non-polar extract.

3. The method of claim 2 wherein said non-polar extract is extracted using one or more solvents selected from the group consisting of $C_1$-$C_8$ alkanes and chloroform.

4. The method of claim 2 wherein said extract comprises a non-polar extract of *Lilium siberia* bulb.

5. The method of claim 2 wherein said extract comprises a non-polar extract of *Lilium siberia* flower.

6. The method of claim 1 wherein said extract comprises a polar extract.

7. The method of claim 6 wherein said polar extract is extracted using one or more solvents selected from the group consisting of water, ethanol, and methanol.

8. The method of claim 6 wherein said extract comprises a polar extract of *Lilium siberia* bulb.

9. The method of claim 6 wherein said extract comprises a polar extract of *Lilium siberia* flower.

10. The method of claim 1 wherein said applying step comprises applying a composition comprising a carrier and from greater than zero to about 20% of said extract to skin in need of skin lightening treatment.

11. The method of claim 1 wherein said applying step comprises applying a composition comprising a carrier and from about 0.1 to about 5% of said extract to the skin in need of skin lightening treatment.

12. The method of claim 1 wherein said applying step comprises applying a composition comprising said extract and a carrier to the skin, said composition being in the form of a solution, suspension, lotion, cream, serum, gel, stick, spray, ointment, liquid wash, soap bar, shampoo, hair conditioner, paste, foam, powder, mousse, shaving cream, hydrogel, or film-forming product.

13. The method of claim 12 wherein said applying step comprises transferring said composition from a substrate to the skin.

14. The method of claim 13 wherein said substrate comprises a wipe or facial mask.

15. The method of claim 1 wherein the applying step comprises applying a composition comprising said extract and an additional skin lightening active agent to the skin.

16. The method of claim 15 wherein said applying step further comprises transferring said composition from a substrate to the skin.

17. The method of claim 16 wherein said substrate comprises a wipe or facial mask.

18. The method of claim 1 further comprising the steps of applying to skin in need of skin lightening a composition comprising said extract once or twice daily for at least 2 weeks.

19. The method of claim 1 wherein said method comprises applying two or more different compositions comprising said extract to the skin in need of skin lightening.

20. The method of claim 19 wherein said two or more different compositions comprising said extract are independently selected from the group consisting of lotions, cleansers, masks, essence, wipes, creams, serums, and gels.

21. The method of claim 20 wherein one of said two or more different compositions is a cleanser and another of said two or more different compositions is a lotion or cream.

22. The method of claim 20 wherein said method comprises applying at least three different compositions comprising said extract to skin in need of skin lightening, said compositions being selected from the group consisting of cleansers, lotions, creams, essences, and facial masks.

* * * * *